(12) United States Patent
Gyöngy et al.

(10) Patent No.: US 9,766,263 B2
(45) Date of Patent: Sep. 19, 2017

(54) APPARATUS AND METHOD FOR DETECTING DISEASE IN DAIRY ANIMALS

(75) Inventors: István Gyöngy, South Queensferry (GB); Robert Eric Boyce, South Queensferry (GB); Antonia Catherine White, South Queensferry (GB)

(73) Assignee: ICEROBOTICS LTD, South Queensferry (GB)

( * ) Notice: Subject to any disclaimer, the term of this patent is extended or adjusted under 35 U.S.C. 154(b) by 906 days.

(21) Appl. No.: 13/695,504

(22) PCT Filed: Apr. 28, 2011

(86) PCT No.: PCT/GB2011/050857
§ 371 (c)(1),
(2), (4) Date: Feb. 4, 2013

(87) PCT Pub. No.: WO2011/135381
PCT Pub. Date: Nov. 3, 2011

(65) Prior Publication Data
US 2013/0138389 A1 May 30, 2013

(30) Foreign Application Priority Data

Apr. 30, 2010 (GB) .................................. 1007291.6

(51) Int. Cl.
*G01P 15/00* (2006.01)
*A61B 5/11* (2006.01)
(52) U.S. Cl.
CPC ............ *G01P 15/00* (2013.01); *A61B 5/1118* (2013.01); *A61B 2503/40* (2013.01); *A61B 2562/0219* (2013.01)
(58) Field of Classification Search
CPC .... G01P 15/00; A61B 2503/40; A61B 5/1118; A61B 5/11
See application file for complete search history.

(56) References Cited

U.S. PATENT DOCUMENTS

| 7,335,168 B2 | 2/2008 | Rugg |
| 8,460,219 B2 * | 6/2013 | Miyake ................. A61B 5/112 600/595 |

(Continued)

FOREIGN PATENT DOCUMENTS

| GB | 2437250 | 10/2007 |
| WO | 2006/015372 | 2/2006 |

(Continued)

OTHER PUBLICATIONS

Pastell et al., A wireless accelerometer system with wavelet analysis for assessing lameness in cattle, Sep. 2009,Biosystem Engineering, 1537-5110, p. 545-551.*

(Continued)

*Primary Examiner* — John Breene
*Assistant Examiner* — Mohammad Islam
(74) *Attorney, Agent, or Firm* — Nixon & Vanderhye PC

(57) ABSTRACT

Disclosed is apparatus and a method for detecting udder disease in dairy animals. An accelerometer is attached to each of a plurality of dairy animals. A processor determines a measure of the activity of the dairy animals to which the accelerometers are attached. Data is recorded by and automatically transmitted from a sensor unit secured to an animal, without the requirement for costly and time consuming chemical analysis of milk, or of visual or veterinary inspection of individual animals in a herd. The development of an udder disease in a dairy animal, such as mastitis, may be identified from a decrease in the monitored measure of activity of a dairy animal. A separate baseline measure of activity may be determined for each dairy animal and the activity of a plurality of dairy animals in one or more herds may be taken into account, in order to reduce false positives due to external effects which are not specific to a single dairy animal.

17 Claims, 4 Drawing Sheets

(56) References Cited

U.S. PATENT DOCUMENTS

| | | | |
|---|---|---|---|
| 2004/0064286 A1* | 4/2004 | Levi | G01C 21/12 702/141 |
| 2006/0155172 A1 | 7/2006 | Rugg | |
| 2008/0202445 A1 | 8/2008 | Rugg | |
| 2008/0288200 A1 | 11/2008 | Noble | |
| 2008/0312511 A1* | 12/2008 | Osler | A61B 5/0008 600/300 |
| 2009/0048498 A1* | 2/2009 | Riskey | A61B 5/0031 600/302 |
| 2009/0182207 A1* | 7/2009 | Riskey | A61B 5/0031 600/302 |
| 2009/0187392 A1* | 7/2009 | Riskey | A01K 11/007 703/11 |
| 2010/0030036 A1* | 2/2010 | Mottram | A01K 11/00 600/301 |
| 2010/0058989 A1 | 3/2010 | Ohman et al. | |
| 2010/0234775 A1* | 9/2010 | Yasuhara | A61H 3/00 601/33 |
| 2010/0331739 A1* | 12/2010 | Maltz | A61D 17/008 600/588 |
| 2011/0276304 A1* | 11/2011 | Yin | A61B 5/1118 702/141 |
| 2011/0298619 A1* | 12/2011 | O'Hare | A01K 11/008 340/573.1 |

FOREIGN PATENT DOCUMENTS

| | | |
|---|---|---|
| WO | 2007/104124 | 9/2007 |
| WO | WO 2008/066440 | 6/2008 |
| WO | 2008/124481 | 10/2008 |
| WO | WO 2008/139448 | 11/2008 |
| WO | 2009/011641 | 1/2009 |
| WO | WO 2010/066429 | 6/2010 |

OTHER PUBLICATIONS

Grohn et al., Effect of Pathogen-Speceific Mastities on Milk Yield in Dairy Cows, Nov. 2003,American Dairy Science Association, 2004, J.Dairy Sci.87:, p. 3358-3374.*

Forschung et al., A system for determing the physical activity of a living animal, Sep. 2007,DE202007010056.*

Martiskainen et. al.,Cow behaviour pattern recognition using a three-dimensional accelerometer and support vector machines, 2009, pp. 32-38.*

Cornou et al.,Classifying sows' activity types from acceleration patterns An application of the Multi-Process, Aug. 2007, pp. 262-273.*

Pastell et al., A wireless accelerometer system with wavelet analysis for assessing lameness in cattle,2009, pp. 545-551.*

International Search Report for PCT/GB2011/050857 mailed Jul. 22, 2011.

Y T Grohn et al, "Effect of Pathogen-Specific Clinical Mastitis on Milk Yield in Dairy Cows", Journal of Dairy Science, American Dairy Science Association, vol. 87, No. 10, Oct. 1, 2004, pp. 3358-3374.

Grohn Y. T. et al.: "Effect of Pathogen-Specific Clinical Mastitis on Milk Yield in Dairy Cows", Journal of Dairy Science, American Dairy Science Association, US, vol. 87, No. 10, Oct. 1, 2004, pp. 3358-3374.

* cited by examiner

APPARATUS AND METHOD FOR DETECTING DISEASE IN DAIRY ANIMALS

This application is the U.S. national phase of International Application No. PCT/GB2011/050857 filed 28 Apr. 2011 which designated the U.S. and claims priority to GB 1007291.6 filed 30 Apr. 2010, the entire contents of each of which are hereby incorporated by reference.

FIELD OF THE INVENTION

The invention relates to the detection of disease, and in particular udder disease such as mastitis, in dairy animals.

BACKGROUND TO THE INVENTION

The present invention relates to a method and apparatus for the automatic detection of udder diseases, such as mastitis, in dairy animals.

Early detection and ongoing monitoring of the health and welfare of dairy animals is imperative. Individual dairy animals suffering from an udder disease typically produce milk of lower quality and/or quantity. Furthermore, illness spreading throughout a dairy herd can significantly impact the output of the herd as a whole.

For example, mastitis is widely recognised as one of the top three most common and costly health conditions affecting dairy animals, along with lameness and fertility management. Estimates put the cost of mastitis alone to UK dairy farms at more than £160 million per annum and the actual cost may be significantly higher, due to unrecorded or undiagnosed cases.

It is estimated that in herds without effective mastitis control, approximately 40% of dairy animals can be infected in two quarters of the udder.

Mastitis is generally indicated by an increase in somatic cell count (SCC) in the milk. A low level of SCC is used as an indicator of good quality milk and can attract a price premium.

Clinical mastitis will manifest itself through changes in the composition of the milk and inflammation of the udder, which will be visually apparent. As well as the pain and discomfort to the animal, reduced milk yield and quality will result. As the infection worsens, costs are also incurred through vet treatment, discarded milk, increased labour costs and ultimately the culling and replacement of stock.

Due to these costs, mastitis is one of the top three reasons dairy animals are culled.

Even sub-clinical mastitis (i.e. lower levels of infection which may not be visually apparent during routine observations of the dairy animal) can reduce the value of the milk.

If diagnosed early, then self-healing is possible with simple hygiene routines, however this may not be possible by the time the disease has progressed far enough to be detected by visual inspection.

Known early mastitis detection methods are either labour intensive or expensive to automate. For example, the condition of the teat may be monitored by measuring electrical conductivity. Although reasonably easy to implement, this method typically offers poor detection performance.

Alternatively, the chemical composition of the milk may be analysed to measure SCC or lactate dehydrogenase levels. Chemical testing of milk may be economically practical at herd level with bulk milk sampling, but is extremely expensive and labour intensive to implement for individual animals.

Therefore, there remains a need for reliable automated identification of potential cases of diseases such as mastitis and/or or of other health and welfare conditions in dairy animal herds at an early stage, in a cost effective manner.

By dairy animals we mean animals used in agriculture for the production of milk for human consumption, including but not limited to dairy cows, goats, buffalo, sheep, horses and camels.

SUMMARY OF THE INVENTION

According to a first aspect of the present invention there is provided apparatus for detecting udder disease in dairy animals, the apparatus comprising an accelerometer for attachment to a dairy animal and a processor operable to determine a measure of activity of a dairy animal to which the accelerometer is attached.

We have found that when the measure of the activity of the dairy animal changes, as measured by an accelerometer, this is indicative that the dairy animal may have a health condition. In particular, we have found that a change, for example a decrease, in activity of a dairy animal may indicate that the animal is suffering from an udder disease such as mastitis. The decrease (or increase, where appropriate) in activity can be indicative of the severity of the disease.

The invention extends in a second aspect to a method of determining the presence of an udder disease in a dairy animal, comprising determining a measure of activity of the dairy animal using an accelerometer attached to the dairy animal, and determining that the dairy animal has (or may have) a udder disease from a change (for example a decrease) in the measure of activity of the dairy animal.

The method may comprise attaching an accelerometer (or a sensor unit comprising the accelerometer) to the dairy animal.

The invention extends to determining the presence of health conditions in dairy animals from a change in the measure of activity of the dairy animal.

The method may comprise determining an acceptable measure of activity, or acceptable range of a measure of activity, of the dairy animal over one or more first periods and determining that the dairy animal has (or may have) an udder disease from a change in the measure of activity of the dairy animal from the acceptable measure, or acceptable range of the measure, during one or more second periods.

The apparatus may comprise a health condition detection module, operable to determine an acceptable measure of activity or an acceptable range of the measure of activity, of the dairy animal over one or more first periods, and operable to determine that a dairy animal has (or may have) an udder disease from a change in the measured of activity of the dairy animal from the acceptable measure, or acceptable range of the measure (as determined from the one or more first periods), during one or more second periods (for example a change in the measure of activity during a second period by a predetermined amount from the acceptable measure of activity or acceptable range of the measure).

The acceptable measure, or acceptable range of the measure of activity, may be determined taking into account one or more of: the time of day, or the time of year, or an activity which is currently being carried out, or known health conditions of the dairy animal. For example, an acceptable measure of activity of a dairy animal during milking (by which we mean to include herding animals to and from a milking parlour) is typically greater than the measure of activity at other times. The acceptable measure of activity or the acceptable range of the measure of activity may vary depending on the time of year, weather conditions, temperature and so forth. If a dairy animal has been identified as suffering from lameness or pregnancy or some other health condition, activity may be reduced or modified as a consequence. If such modifications to activity are not taken into account, this may cause changes in a measure of activity to be erroneously attributed to udder disease, or may result in changes in a measure of activity due to a udder disease being erroneously attributed another known or obvious health condition (or external stimulus). Whereas, taking known health conditions or external stimuli into account may therefore enable such erroneous attribution of a change in a measure of activity to be avoided.

The method may comprise monitoring a measure of the activity of one or more further dairy animals, which may be within the same herd as the dairy animal. The apparatus may comprise a plurality of accelerometers for determining a measure of the activity of one or more further dairy animals. Each accelerometer may have a separate processor associated therewith or one processor may determine a measure of the activity of each of a plurality of dairy animals to which a respective plurality of accelerometers are attached, In some embodiments, a measure of the activity of all of the dairy animals in a herd of dairy animals is monitored. In some embodiments, a measure of the activities of one or more dairy animals from one or more further herds is also monitored.

Monitoring a measure of the activity of one or more further dairy animals enables the early identification of the spread of disease within a herd or between herds. Additionally, monitoring a measure of the activity of one or more further dairy animals enables fluctuations of activity throughout a group or herd of animals to be correlated. For example, activity across a herd may change as a result of external stimuli such as fear, weather, feeding, noise, etc. and a change in a measure of the activity of an animal correlating to a corresponding general change in activity across an entire herd (which would not be indicative of a health condition of the said animal) may be distinguished from a change in a measure of the activity of an animal which does not correlate with a similar change in the activity across an entire herd (which may indicate that the said animal is suffering from a health condition, such as an udder disease).

Thus, the acceptable measure of activity, or acceptable range of a measure of activity, of the dairy animal may be determined taking into account the measure of activity of one or more or all of the one or more further dairy animals (which are preferably part of the same herd as the dairy animal) using respective accelerometers. This reduces the risk of false detections that a dairy animal has an udder disease.

The apparatus may comprise a central data receiving unit, operable to receive data relating to the activity of the or each dairy animal, from one or more sensor units, each said sensor unit secured (or securable) to a dairy animal and comprising an accelerometer (or, in some embodiments one or more further motion sensors, each of which may be an accelerometer or an alternative type of motion sensor such as a gyroscope or an inertial sensor such as a pedometer). Each said sensor unit may comprise a processor. Alternatively, or in addition, the central data receiving unit may be in communication (wired or otherwise) with a central processor.

The data receiving unit may receive and store activity related data, for example, output data from the or each said accelerometer. The data receiving unit may receive activity related data from the or each processor. The central processor may be operable to process or further process the received activity related data.

Activity related data received by the data receiving unit may be data indicative that an animal may have an udder disease, such as mastitis. The sensor unit may comprise the processor and may be operable to process movement data received from the or each movement sensor and generate activity related data, which may be indicative that an animal has an udder disease. The data receiving unit may be operable to process or further process the activity related data to determine that an animal has an udder disease.

The activity related data which may be acceleration data, raw or otherwise, or may be activity related data obtained by processing acceleration data (processed by the processor of each said sensor unit).

In some embodiments, the data receiving unit is operable to receive activity related data from a plurality of sensor units secured to a plurality of dairy animals. In some embodiments, activity related data is received by the data receiving unit from several herds, for example across the internet or other network (for example from other data receiving units connected to the internet). Acquisition of activity related data from other herds enables activity data and patterns of activity data to be more accurately correlated to confirmed health conditions, such as an udder disease, thus enabling more accurate identification of future health conditions. Sharing of data between herds advantageously facilitates early identification of health conditions transmissible between herds. Thus, the apparatus may comprise an input interface (for example a user interface or data interface) for receiving data concerning health conditions diagnosed in dairy animals, for example, by vets or farmers, and may take that received data into account when subsequently determining the acceptable measure of activity of the diagnosed dairy animal, or one or more other dairy animals.

Thus, the method may comprise receiving diagnoses of health conditions in individual dairy animals, correlating those diagnoses with measures of activity recently made by an accelerometer attached to the respective dairy animal, and taking that into account when subsequently determining the acceptable measure of activity of the diagnosed dairy animal, or one or more other dairy animals.

A sensor unit is typically secured or securable to a dairy animal by way of a fixture, such as a strap, but could be implanted or implantable into the dairy animal. The sensor unit may be operable to transmit (via a transmitter or a tranceiver) activity related data, or processed data indicative that the dairy animal may be suffering from an udder disease, to a data receiving unit.

The or each accelerometer may be a multi-axis accelerometer and is preferably a three-axis accelerometer. The or each accelerometer may be integrated with other components, for example the processor.

Preferably, the or each accelerometer is operable to identify motion which does not involve net horizontal displacement of a dairy animal, for example, kicking, standing, lying or feeding.

This may be achieved, for example, where the or each accelerometer is attached to a leg of the dairy animal, or to the neck (enabling feeding activity to be determined). Typically, the or each accelerometer can also identify motion which does involve the net horizontal displacement of a dairy animal, for example, walking.

Advantageously, data from an accelerometer operable to distinguish motion in more than one direction may be used to distinguish between different activity types. For example, data obtained from a two or three axis accelerometer may be processed to identify activity characteristic of walking or feeding of a dairy animal from activity indicative of standing or lying, or transition between standing or lying. The apparatus may therefore be operable to detect one or more activity types and, in some embodiments, the processor may be operable to calculate one or more parameters associated with the or each said activity type and thereby determine a measure of the or each said activity type.

Thus, the data from the accelerometer may be analysed by the processor to determine a measure of an activity type. For example, it may be determined that the activity type is standing, or lying, or transitioning between standing and lying, or walking, or feeding. The data may be analysed by the processor to determine a measure of the activity type such as the proportion of time spent by an animal in a first and at least one second activity type. The data may be analysed to extract one or more further, or alternative measures of activity associated with the or each activity type; for example step count, frequency of a said activity type (e.g. number of times an animal lies down, number of times or frequency that an animal kicks), average duration of a said activity type, an index value associated with kinetic energy expended by the animal during a said activity type (during a particular period, or an average or summarised value relating to several periods during which an animal exhibited a said activity type).

The measure of activity of a dairy animal may be determined from the kinetic energy transmitted to an accelerometer by a dairy animal, advantageously after removing the offset due to gravity. Kinetic energy, or activity related data related to kinetic energy may be summed over a period of time, or averaged. Where the accelerometer is part of a sensor unit attached to or for attachment to a dairy animal, a parameter related to (e.g. proportional to) the kinetic energy transmitted to the accelerometer may be calculated within the sensor unit and transmitted to a central data receiving unit for further analysis.

In one embodiment, the apparatus comprises a two axis, or a three axis accelerometer secured to a leg of a dairy animal, and the processor is operable to distinguish motion associated with walking, and thereby compute a step count, and operable to calculate an index value related to the total amount of energy expended by the animal, from absolute values of acceleration (said values preferably corrected for corrected for gravity offset).

Preferably, the apparatus is operable to calculate (from accelerometer data) an index value related to the amount of energy expended by the animal and operable to determine a measure of at least one activity type. The index value may be associated with the total energy expended, or average energy expended, or the average or total associated with one or more specified activity types or one or more specified periods (which may be periods associated with an occurrence of a specified activity type). The measure of at least one activity type may be associated with the same or a different period or activity type, as the case may be.

In some embodiments, the accelerometer is operable to distinguish the time taken between, or the rate of, certain activities. For example, apparatus operable to distinguish standing up and lying down may be operable to determine the length of time that an animal takes to stand up and lie down, and/or the number of times that an animal lies down. An animal suffering from a disease may take longer to stand up and lie down than a healthy animal, and/or may seek to lie down more frequently or for longer durations. Thus, such transition times and/or lying down frequency/duration may be characteristic of a disease, e.g. an udder disease such as mastitis.

In use, two, or more than two movement sensors may be secured to the or each said dairy animal, and may be secured to different parts of the body of the or each said dairy animal. For example, a dairy animal may be equipped with a movement sensor such as an accelerometer on a leg (typically a hind leg) and a second sensor in the region of the head or neck (for example, an ear tag may comprise a sensor), so as to enable activity associated with feeding to be distinguished from activity associated with walking or kicking.

Data indicative that a dairy animal is feeding (for example obtained from a motion sensor secured in the head or neck region of a dairy animal) may be correlated with feeding time information, or data indicative that a dairy animal is feeding may be correlated with data from other dairy animals, so as to identify whether the feeding activity of the said dairy animal is indicative of a possible health condition.

Accordingly, the invention extends in a third aspect to a method of detecting a health condition in a farm animal, comprising determining a first measure of activity, and at least one second measure of activity, of the animal using an accelerometer attached to the animal, and determining that the animal may have (or has) a health condition from a change in the first measure, taking into account at least one said second measure.

The first measure may be a measure of the overall activity of an animal (for example over a predetermined period or periods) or may be a measure of an activity type.

The or each said second measure may be a measure of the overall activity of an animal (for example over a predetermined period or periods) or may be a measure of an activity type.

The method may comprise determining a first measure of a first activity type, and at least one second measure of a second activity type, of the animal using an accelerometer attached to the animal, and determining that the animal may have (or has) a health condition from a change in the first measure, taking into account at least one said second measure.

A measure of activity type (e.g. the second measure) may be a measure of the amount (instances counted in a period of time), frequency or duration of a type of activity.

The method may comprise attaching an accelerometer (or a sensor unit comprising the accelerometer and, in some embodiments a processor) to the animal.

For example, the accelerometer may be a multi-axis accelerometer, operable to output activity related data to a processor (which may be integral to a sensor unit attached to the animal) and the processor may be operable to process the data so as to distinguish a first activity type (for example, walking or other activity resulting in a net horizontal displacement of the animal) from a second activity type (for example, standing and/or lying and/or kicking and/or other activities resulting in substantially no net horizontal displacement of the animal). In some instances, determining that an animal has or may have a health condition may be achieved more reliably and with greater sensitivity (by which we mean, when the health condition is less severe, or at an earlier stage of progression) or greater specificity (i.e. with fewer false positives) by taking into account at least one second measure of activity.

The method may comprise attaching an accelerometer and a further motion sensor to an animal (of the same or a different type, such as a magnetometer or a gyroscope), typically to a different part of the animal. For example a motion sensor attached to the head or neck region of the animal may be operable to measure feeding activity and the accelerometer may be operable to measure one or more other types of activity.

The method may be a method of detecting one or more of the following health conditions, or may be a method of detecting a health condition or detecting mastitis in a dairy animal by taking into account one or more of the following health conditions: foot and mouth disease (or other hoof and foot diseases, such as digital dermatitis), bovine tuberculosis, ketosis (or other metabolic conditions), lameness, oestrus, uterus and reproductive organ disease, mastitis, bluetongue, bovine tuberculosis, bovine virus diarrhoea (BVD), salmonella, digestive diseases and infectious bovine rhinotracheitis (IBR), African swine fever virus (ASFV), classical swine fever virus (CSFV), peste de petits ruminants virus (PPRV).

The invention extends in a fourth aspect to apparatus for detecting a health condition in a farm animal, comprising an accelerometer for attachment to a farm animal, operable to output activity related data to a processor, and a processor operable to determine a first measure of activity and at least one second measure of activity, of the animal to which the accelerometer is attached, from the received activity related data. The apparatus may alternatively comprise an accelerometer for attachment to a farm animal, operable to output data related to a first measure of activity of the animal, and at least one further motion sensor for attachment to a farm animal (typically to a different part of the animal to the accelerometer), operable to output data related to at least one second measure of activity of the animal, and a processor (or in some embodiments more than one processor) operable to determine a first measure of activity and at least one second measure of activity of the animal from the said activity related data.

Preferred and optional features of the method of the third aspect correspond to preferred and optional features of the method of the second aspect. Preferred and optional features of the apparatus of the fourth aspect correspond to preferred and optional features of the apparatus of the first aspect.

In embodiments wherein the or each said sensor unit comprises a transmitter, the transmitter may be a passive transmitter, such as an RF transceiver powered by electromagnetic induction, such that data relating to an animal's activity is transmitted from the unit when the animal passes a receiver operable to inductively power the passive transmitter (such as an RF-antenna). The receiver may be in wired, or wireless, communication with the data receiving unit.

For example, a milking parlour may be provided with an inductive power generating RF reader (comprising an RF-antenna) at an entrance thereof, such that a sensor unit secured to a dairy animal entering the milking parlour is inductively powered and caused to transmit activity related data.

In some embodiments, the sensor unit is operable between a dormant mode and an active mode, wherein, in the dormant mode the unit does not transmit activity related data and (in some embodiments does not acquire activity related data) in the active mode, the unit transmits (and, in some embodiments, records) activity related data and wherein the sensor unit is caused to switch from the dormant to the active mode when it is brought within a predetermined distance of the receiver.

The sensor unit may comprise a transceiver operable to communicate, when the sensor unit is in a dormant mode, with the receiver. The sensor unit may alternatively or additionally comprise a transmitter operable to transmit activity related data to the data receiving unit, when the sensor unit is in an active mode. The sensor unit may comprise a motion data storage unit, operable to store data acquired when the sensor unit is dormant, for transmission when the sensor unit is active. Thus, in some embodiments, the sensor and (where present) the motion data storage unit functions when the sensor unit is dormant and active (such that motion data is acquired when the sensor unit is dormant and active), and in some embodiments, the sensor functions only when the sensor unit is active (such that motion data is only acquired when the sensor unit is active).

In some embodiments, the method of the second or third aspects comprises the step of estimating somatic cell count. For example, the method may comprise milking a dairy animal, measuring somatic cell count in the milk, correlating the measured somatic cell count with activity data measured during a period preceding the milking, and taking the measurement into account when estimating somatic cell count from activity measured during a subsequent period.

The invention also extends in a fifth aspect to computer software comprising program instructions which, when executed on a processor, cause the processor to determine from activity related data received from an accelerometer and/or one or more further movement sensors, whether an animal (such as a dairy animal) has a health condition (for example an udder disease, such as mastitis), from a change in a measure of activity of the animal from an acceptable measure of activity, or acceptable range of the measure of activity. Further steps which the program instructions optionally cause the processor carry out when they are executed are set out above in respect of the first through fourth aspects of the invention. For example, the program instructions, when executed on a processor, typically cause the processor to determine an acceptable measure of activity or acceptable range of the measure of activity for a dairy animal taking into account the measured of activity of one or more other dairy animals. For example, the program instructions, when executed on a processor, may cause the processor to determine an acceptable measure of a first activity type or an acceptable range of the measure of a first activity type of a farm animal taking into account a measure of at least one second activity type.

The invention extends to a computer readable medium having the computer software stored thereon or therein.

DESCRIPTION OF THE DRAWINGS

An example embodiment of the present invention will now be illustrated with reference to the following Figures in which.

DETAILED DESCRIPTION OF AN EXAMPLE EMBODIMENT

Figure 1:
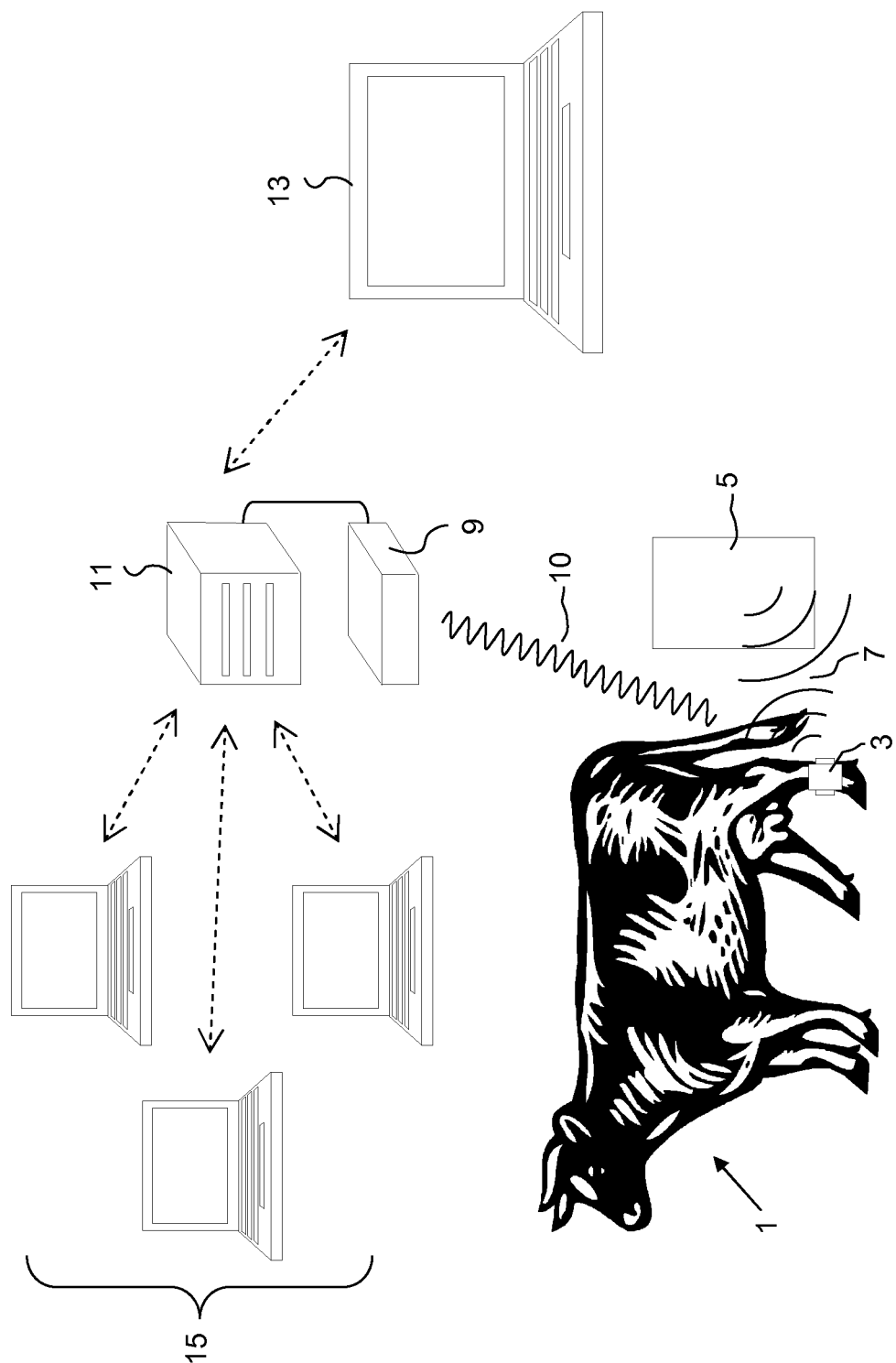
FIG. 1 is a schematic diagram of apparatus for detecting udder diseases in cattle.

An example of apparatus according to the invention is shown schematically in FIG. 1. A cow 1 is provided with a sensor unit 3, strapped to a hind leg. The sensor unit comprises a low power, low radio frequency transceiver, and a high power, high radio frequency transmitter, a three axis accelerometer (functioning as a motion sensor), a motion data storage unit and a battery.

The sensor unit is operable to store motion data measured by the accelerometer in use and to transmit it to a central receiver 9. In an example embodiment, the sensor unit is operable between a dormant mode, wherein the transceiver, accelerometer and motion data storage unit is functional, and a higher power active mode, wherein the accelerometer, motion data storage unit and the transmitter are functional. When brought into the proximity of a tablet reader 5 (typically positioned at an entrance to a milking parlour) the sensor unit communicates with the tablet reader via low power, low radio frequency signals 7 to transmit the stored data. The sensor unit is thus caused to switch from a low power dormant mode to a high power active mode, in which the transmitter transmits stored motion data acquired when the sensor unit was dormant) to a central receiver 9 by high power, high radio frequency signals 10 and, optionally transmits (continuously or periodically) motion data for a further period of time, after which the sensor reverts to a dormant mode. Optionally, further communication with the tablet reader (for example when exiting the milking parlour) causes the sensor unit to revert to a dormant mode. The duration for which the sensor unit is in an active mode is thus minimized and battery life thereby optimised.

The receiver is in wired communication with a server 11 (function as a data receiving unit) which communicates wirelessly (or, in some embodiments, over a wired connection) with a laptop computer 13 running data processing software (thus functioning as a processor).

The server is also optionally in wireless communication (or in communication over the internet) with further computers 15 located remotely (typically each in communication with sensors secured to cows of different herds).

The server monitors motion data from each of a plurality of cows and calculates a motion index for each cow (wherein the motion index is a measure of activity). The motion index is the sum of the measured net acceleration (minus an offset for gravity) to which a sensor unit attached to a respective cow is subjected, summed over a period of time, and is therefore representative of the kinetic energy transferred to the sensor unit by the cow to which it is attached.

In some embodiments, the data measured by the accelerometer is transmitted to the central receiver and forwarded to the server in raw form. Thus, the server calculates the motion index. In alternative embodiments, the sensor unit comprises a processor which receives the motion data and generates activity related data, derived from the raw motion data, to be transmitted to the receiver. Thus, in these embodiments, the sensor unit calculates the motion index.

The motion index associated with a cow is monitored over an extended period of time. The time averaged value of the motion index is periodically compared with a threshold value, functioning as acceptable motion. If the time average value of the motion index drops below the threshold for an extended period of time, an alert is generated by the server that the cow in question may be suffering from a health condition, such as mastitis.

When determining the threshold value, the server takes into account corresponding values of the motion index calculated in respect of other cows in the herd. Thus, external factors which affect the entire herd can be taken into account, reducing false alarms. Values of the motion index calculated in respect of cows in other herds can also be taken into account to further improve the reliability of alerts.

It may be that only the motion index calculated during certain activities, e.g. milking, or at certain times of the day is taken into account.

Use of the apparatus was demonstrated in a number of experiments. In a first experiment, four lactating Holstein-Friesian cows were each fitted with sensor units comprising a three axis accelerometer on both of the rear legs. The sensor units were IceTag3D devices available from IceRobotics Limited of South Queensferry, United Kingdom.

The cows were separated from herd on day one and were given three days to settle into their new pen. The animals were milked each morning and each afternoon (at approximately 7:00-7:30 am and 15:30-16:00 pm, respectively) on each day of the experimental period.

They were infected with mastitis, by injecting *Streptococcus uberis* into two udder quarters, after scheduled afternoon milking on day four. The cows were observed for four further days before being treated with antibiotics after the scheduled morning milking of day eight.

The specific time period over which the effect of the illness was considered was from midday of day four to midday on day eight. The observational period therefore included eight milkings.

One of the cows was later diagnosed with a pre-existing *Staphylococcus aureus* infection, and went on to develop acute mastitis on day five. Data concerning this animal was therefore excluded from the data analysis. A tag on a second animal developed a fault during the observational period and the corresponding data was also disregarded.

Somatic cell count and bacteriological level in milk samples from each udder quarter of three cows were taken at the eight milkings, during the observational period, and are shown in Table 1. Bacteriology data are presented in colony forming units/ml, somatic cell count data are present in cells/µl.

TABLE 1

Results of milk analysis
(average figures for all four quarters of each animal)

| Day/milking | | Dairy animal 7159 | | Dairy animal 7189 | | Dairy animal 7387 |
| | Bacteriology | Somatic cell count | Bacteriology | Somatic cell count | Bacteriology | Somatic cell count |
|---|---|---|---|---|---|---|
| 4 pm | 0 | 41.25 | 0 | 63 | 0 | 18.25 |
| 5 am | 0 | 16.25 | 85 | 42.75 | 5 | 13.75 |
| pm | 0 | 35.5 | 325 | 58.5 | 0 | 21.25 |
| 6 am | 0 | 13 | 25050 | 42.25 | 30 | 10.5 |
| pm | 0 | 44.5 | 2540 | 674.75 | 5455 | 56.25 |
| 7 am | 0 | 19.5 | 100 | 456.5 | 20 | 604 |
| pm | 0 | 35 | 0 | 346 | 0 | 1144.25 |
| 8 am | 0 | 22 | 0 | 254.75 | 0 | 995 |

Data shown in Table 1 indicate that that only two dairy animals out of the three dairy animals of interest were successfully infected (the milk samples from Dairy animal 7159 showing no significant levels of bacteria).

For cows that have not previously suffered from mastitis, a somatic cell count above 100 cells/µl from any udder quarter is considered to be indicative of the disease. The data therefore indicate that the two remaining cows developed mastitis in the second half of the observational period, but that none of the three cows under consideration developed anything beyond sub-clinical mastitis (i.e. low level mastitis, which is typically not identified by visual inspection of the udders).

Figure 2:
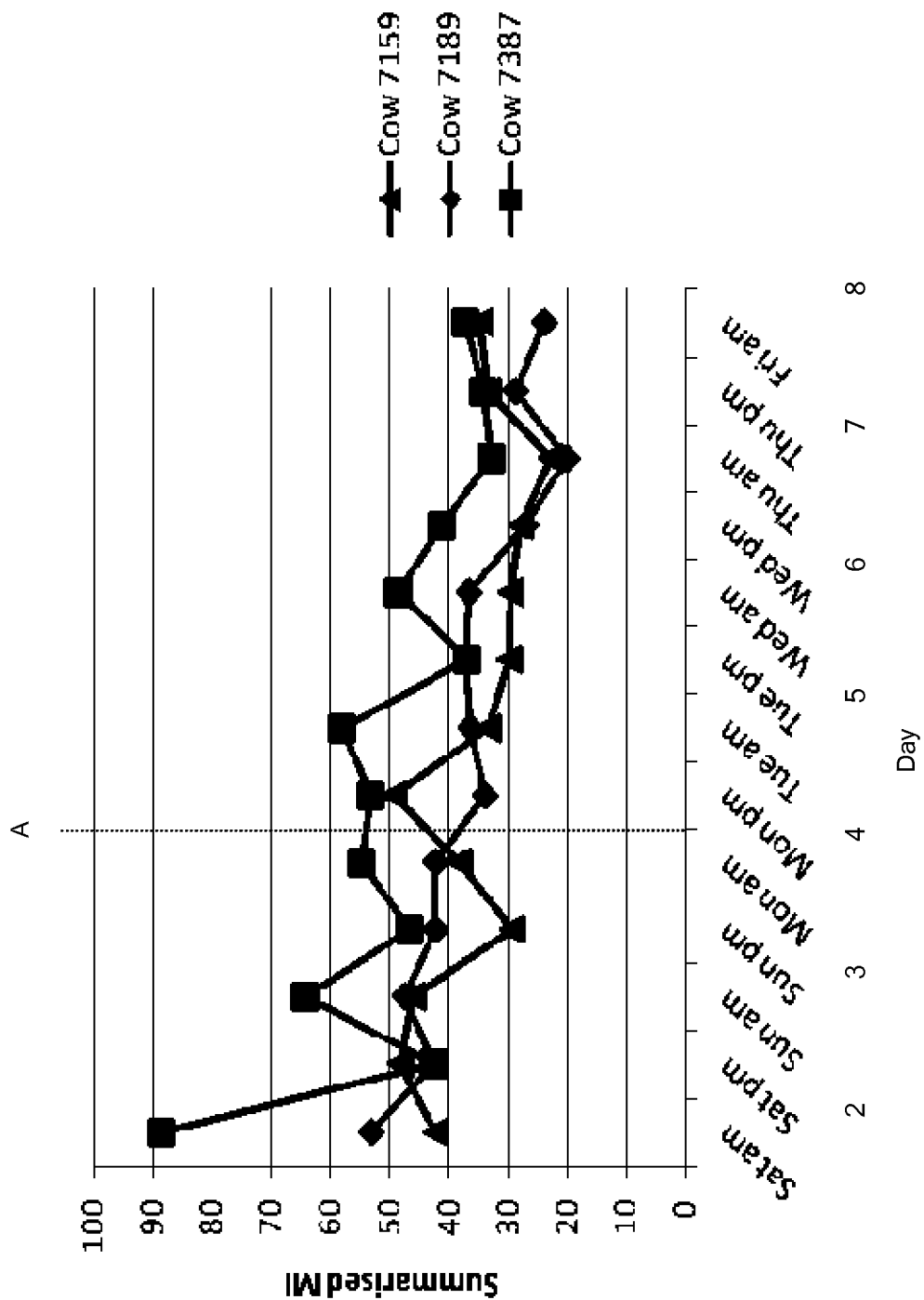
FIG. 2 shows measured activity levels of animals before and during an observation period.

Activity related data was recorded during the observation period (and transmitted by each receiving unit during milking) for a period of 255 minutes before and after transmission was triggered by the reader, immediately prior to milking, is shown in FIG. 2. Data corresponding to each milking period are presented for each animal as a summation motion index (related to total expended by each animal). In alternative embodiments, data is summarised over different periods. For example, in some cases, milking is conducted more, or less frequently, or data may be summarised in units of a calendar day.

Initial elevated activity levels following the relocation of the animals tapers prior to the observational period (beginning at A).

Data during the observational period were fitted to a linear model of Formula A:

$$y_{ijk} = \mu + \text{DAIRY ANIMAL}_i + \beta \log_{10}(\text{SCC}_{ij}) + e_{ijk} \quad \text{(Formula A)}$$

Where:
y is the summarised motion index (MI) (an activity measure), i refers to each of the dairy animals, j=1, 2, 3, . . . , 8 denotes the different milkings during the observational period and k=1, 2 and indicates the leg (left or right) on which the measurement was made on each animal.

Figure 4:
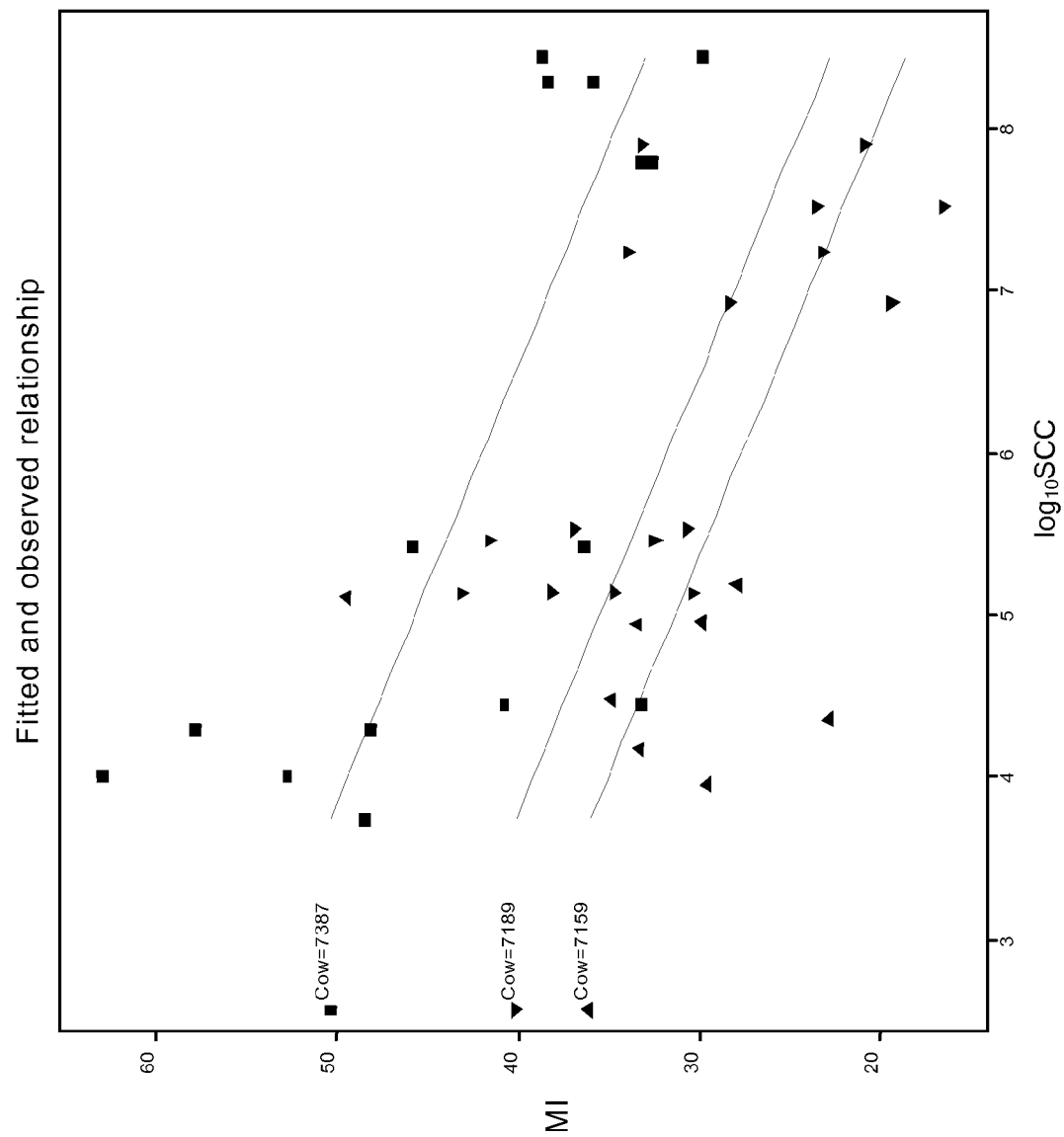
FIG. 4 shows data acquired during the observation period fitted to Formula A.

The model assumes that the activity of a specific dairy animal around a given milking is equal to the sum of:
1) an overall, time-invariant mean activity level μ
2) a dairy animal specific term DAIRY ANIMAL (thus, the model takes into account the natural
variation in activity between individual dairy animals)
3) a term proportional to the logarithm of the somatic cell count (SCC) of the milk
4) a residual term e Statistical analysis based on this model one indicates that SCC has a significant effect on the activity level of an animal, as shown in FIG. 4. In particular, an elevated SCC (indicating mastitis) correlates with lower activity levels.

Figure 3:
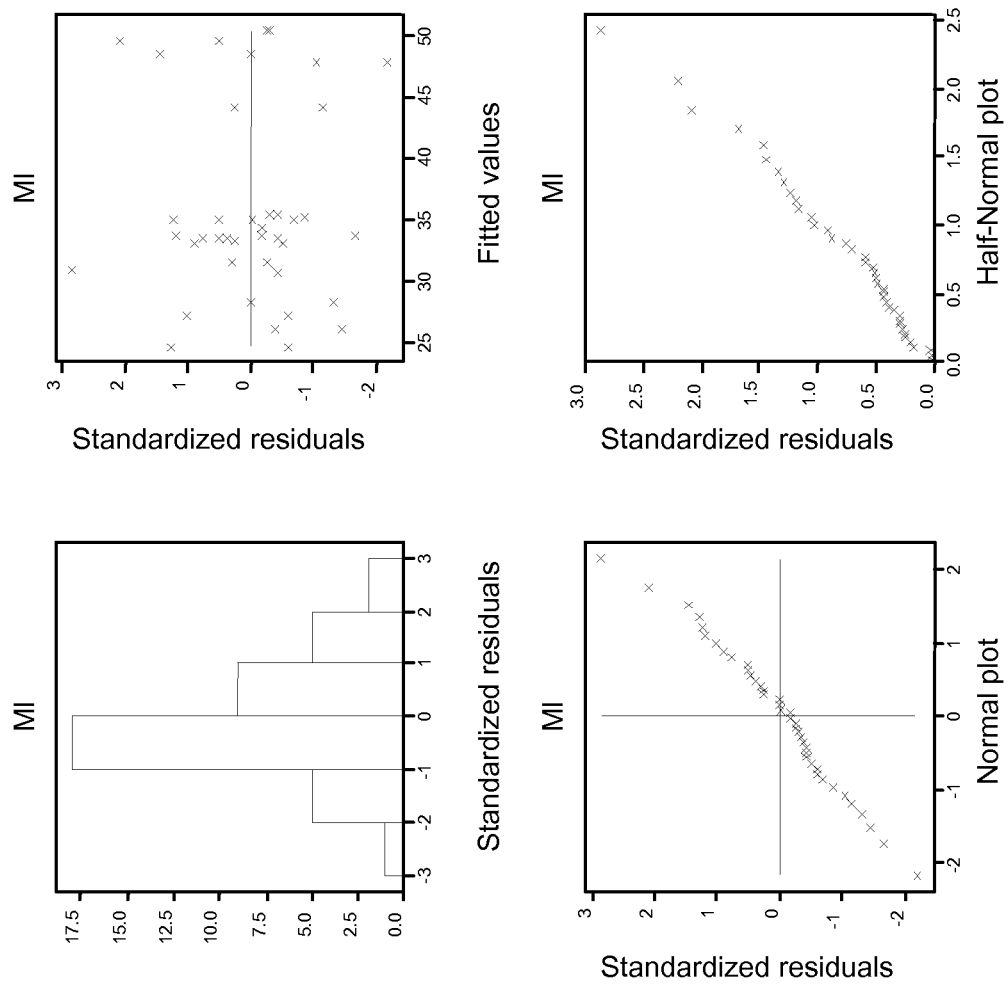
FIG. 3 shows four sub-plots of the residuals of data acquired from three dairy animals during the observation period.

The analysis assumes that the residuals are independent, normally distributed and have constant variance. The last two of these assumptions may be verified using residual plots, which are shown in FIG. 3.

The scatter plot of the residuals versus the predicted values (top-right subplot) shows an approximately even scattering around zero, suggestive of a constant variance.

The bottom sub-plots are normal and half-normal plots, both of which follow a straight line, supporting the assumption of normality.

FIG. 4 shows data acquired during the observation period fitted to Formula A. Straight lines are plotted through the data of each cow, fitted to a scatter plot of Motion Index versus $\log_{10}(\text{SCC})$.

The decrease in activity with high somatic cell count can be clearly seen from the downward slope of the lines.

The step count of each animal (determined from a further analysis of accelerometer data) was also determined, as was a "standing percentage" (percentage of time each animal was standing still during each period).

Using the same type of mathematical model as set out in Formula A, but taking either the standing percentage or the step count as the activity related data, instead of the motion index, no statistically significant evidence of a corresponding correlation between SCC and these alternative measures of activity was shown.

We have also found that the sampling duration either side of each milking, over which the Motion index summed, does not give additional results either. A reduced effect of the variable $\text{DAIRY ANIMAL}_i$ is observed in the model, which may be indicative that shorter sampling durations would be more appropriate following initial installation of the apparatus.

Experimental results show a strong link between mastitis and a fall in activity levels, enabling a correlation between even sub-clinical mastitis to be identified, which may only be detected currently through expensive and time consuming chemical analysis.

Far greater reductions in activity were seen in subsequent trials of animals having acute mastitis, detectable through activity as measured by motion index and, in addition, but also the step count and (in some cases) the standing percentage.

The post relocation data prior to the sampling period also demonstrate that the importance of taking the behaviour of other individuals in a herd (or, a herd average) into account.

In subsequent experimental trials, correlations have been observed between a decrease in activity and both clinical milk score and clinical udder score.

In a further trial, data were acquired for animals in a herd over a period of several months and data concerning ten cases of mastitis (diagnosed conventionally) occurring in seven of the animals was retrospectively analysed in order to test whether the accelerometer data could be processed by the methods of the invention to identify the subsequently observed cases of mastitis.

The parameters of motion index, step count and lying % were calculated from the data for each animal, for a period of one month before and after each diagnosed case of mastitis. (The motion index is a first measure of activity and step count and lying % are each second measures, being measures of activity types).

Daily values were generated for each of:
a 4-day TREND (a rolling value resulting from a linear fit to the previous 4 days of activity data)
a *DIFF value (a daily value calculated from the difference in activity between an average or summation value from the preceding 24 hours as compared to the preceding 6 days)
A range of coarse acceptability criteria were then applied to the values.

Unlike the results shown in FIG. 4, where herd wide behaviour was taken into account by discounting post relocation elevation in the activity of all animals, herd wide behaviour and pre-existing health conditions were not taken into account.

It was observed that all ten instances of mastitis corresponded to periods for which the *DIFF value exceed twice the *std value, however using this simple test, a number of false positives (which may be indicative of herd-wide variations in activity or other health conditions) were also observed, i.e. periods for which the *DIFF value exceeded twice the *std value which did not correspond to an observed case of mastitis. Similarly, it was observed that a TREND value of −5 or less was also found to be indicative of a possible mastitis case.

Thus, it was demonstrated that the data could be used to identify that an animal may be suffering from mastitis.

Further variations and modifications may be made within the scope of the invention herein disclosed.

The invention claimed is:
1. An Apparatus for detecting udder disease in a dairy animal, the apparatus comprising:

at least one accelerometer for attachment to a leg of the dairy animal; and a processor operable to:

determine a measure of activity of the dairy animal to which the accelerometer is attached based on measurements from the accelerometer, wherein the determined measure of activity is a motion index calculated based on a measured net acceleration, minus an offset for gravity, of the accelerometer, summed over a period of time;

determine a measure of feeding of the dairy animal from a second sensor in a region of head or neck of the dairy animal, the measurement from the second sensor distinguishing feeding from activity associated with walking or kicking, and determine that the diary animal has the udder disease from a change in the measure of activity of the dairy animal based on the measurements from the at least one accelerometer and also the measure of feeding of the dairy animal obtained from the second sensor, and thereby detect the udder disease in the dairy animal based upon the determination.

2. The apparatus according to claim 1, comprising a health condition detection module, operable to determine an acceptable of the measure of activity or an acceptable range of the measure of activity, of the dairy animal over one or more first periods, and operable to determine that the dairy animal has or may have the udder disease from the change in the measured of activity of the dairy animal from the acceptable measure, or the acceptable range of the measure, during one or more second periods.

3. The apparatus according to claim 1, comprising a plurality of accelerometers for monitoring the measure of the activity of one or more further dairy animals.

4. The apparatus according to claim 1, comprising a central data receiving unit, operable to receive data relating to the activity of the each dairy animal, from one or more sensor units, each said sensor unit secured or securable to the dairy animal and comprising the accelerometer.

5. The apparatus according to claim 4, wherein each said sensor unit comprises a transmitter, operable to transmit the activity related data to the data receiving unit.

6. The apparatus according to claim 1, wherein the at least one accelerometer is operable to identify motion which does not involve net horizontal displacement of the dairy animal.

7. The apparatus according to claim 1, wherein the at least one accelerometer can identify motion which involves the net horizontal displacement of the dairy animal.

8. The apparatus according to claim 1, wherein the at least one accelerometer is operable to distinguish motion in more than one direction, and wherein data from the at least one accelerometer may be used to distinguish between different types of activity, wherein the different types of activity are selected from a group consisting of: walking, feeding, standing, lying and transitioning between standing and lying.

9. A method of determining a presence of an udder disease in a dairy animal, comprising:

using a computer processor, determining a measure of activity of the dairy animal using at least one accelerometer attached to a leg of the dairy animal, wherein the determined measure of activity is a motion index calculated based on a measured net acceleration, minus an offset for gravity, of the accelerometer, summed over a period of time, determining a measure of feeding activity of the dairy animal from a second sensor in a region of head or neck of the dairy animal, the measurement from the second sensor distinguishing feeding from activity associated with walking or kicking, and determining, that the dairy animal has the udder disease from a change in the measure of activity of the dairy animal based on the measurements from the at least one accelerometer and also the measure of feeding of the dairy animal obtained from the second sensor, and thereby detecting the udder disease in the dairy animal based upon the determination.

10. The method according to claim 9, comprising determining an acceptable of the measure of activity, or an acceptable range of the measure of activity, of the dairy animal over one or more first periods and determining that the dairy animal has or may have an udder disease from the change in the measure of activity of the dairy animal from the acceptable of the measure of activity, or the acceptable range of the measure of activity, during one or more second periods.

11. The method according to claim 10, wherein the acceptable measure of the activity is determined by taking into account one or more of: a time of day, a time of year, or an activity which is currently being carried out, or known health conditions of the dairy animal.

12. The method according to claim 9, comprising monitoring the measure of the activity of one or more further dairy animals to thereby distinguish the change in the measure of activity of the dairy animal from a change in the measure of activity of the one or more further dairy animals.

13. The method according to claim 12, wherein the acceptable measure of activity or the acceptable range of the measure of activity, of the dairy animal may be determined taking into account the measure of activity of one or more of the one or more further dairy animals.

14. The method according to claim 9, wherein one or more further motion sensors is or are secured to the each dairy animal.

15. The method according to claim 9, comprising thereby detecting mastitis using the determined measure of activity of the dairy animal to which the accelerometer is attached.

16. The method according to claim 9, comprising a estimating somatic cell count.

17. A non-transitory computer readable medium encoded with a computer software program which, when executed on a computer processor, causes the computer processor to:

determine a measure of activity of the dairy animal using an accelerometer attached to a leg of the dairy animal, wherein the determined measure of activity is a motion index calculated based on a measured net acceleration, minus an offset for gravity, of the accelerometer, summed over a period of time, determine a measure of feeding activity of the dairy animal from a second sensor in a region of head or neck of the dairy animal, the measurement from the second sensor distinguishing feeding from activity associated with walking or kicking, and determine that the dairy animal has an udder disease from a change in the measure of activity of the dairy animal based on the measurements from the at least one accelerometer and also the measure of feeding activity of the dairy animal obtained from the second sensor, and thereby detect the udder disease in the dairy animal based upon the determination.

* * * * *